(12) United States Patent
Fuhrman

(10) Patent No.: US 8,353,293 B1
(45) Date of Patent: Jan. 15, 2013

(54) CPAP OUTLET VENT GAS DIFFUSER

(76) Inventor: Nancy E Fuhrman, Seattle, WA (US)

( * ) Notice: Subject to any disclaimer, the term of this patent is extended or adjusted under 35 U.S.C. 154(b) by 602 days.

(21) Appl. No.: 12/611,337

(22) Filed: Nov. 3, 2009

(51) Int. Cl.
*A61M 11/00* (2006.01)
(52) U.S. Cl. .............................. 128/206.21; 128/204.18
(58) Field of Classification Search ............ 128/206.21, 128/204.18, 202.27, 205.24; 138/118, 37
See application file for complete search history.

(56) References Cited

U.S. PATENT DOCUMENTS

| | | | |
|---|---|---|---|
| 4,949,733 A * | 8/1990 | Sampson | 128/864 |
| 7,472,706 B2 * | 1/2009 | Weiss | 128/207.17 |
| 2007/0175480 A1 * | 8/2007 | Gradon et al. | 128/207.11 |
| 2008/0295835 A1 * | 12/2008 | Han et al. | 128/204.18 |
| 2009/0272380 A1 * | 11/2009 | Jaffre et al. | 128/202.27 |

* cited by examiner

*Primary Examiner* — Steven Douglas
(74) *Attorney, Agent, or Firm* — Joseph Z. Ellsworth

(57) ABSTRACT

A CPAP vent diffuser adapted to effectively seal around a vent of a CPAP mask comprises a chamber of porous cloth that moderates air flow from the vent of CPAP machine by increasing in the chamber walls the area the air flow has to move through thus decreasing the speed of the air.

13 Claims, 5 Drawing Sheets

CPAP OUTLET VENT GAS DIFFUSER

BACKGROUND

1. Field of the Invention

This invention relates to apparatuses that assist breathing, usually during sleep, such as a CPAP system, that has a mask that covers a user's nose or both mouth and nose. More specifically, the invention relates to a gas diffuser adapted to connect around an outlet vent of the mask through which expired air from the user and an air pressure machine is exhausted.

2. Prior Art

Sleep apnea temporarily closes a user's air ways and causes the user to wake up, even if momentarily, as lack of oxygen is communicated to the brain. This lack of oxygen is dangerous and may cause high blood pressure and other cardiovascular disease, stroke, memory problems, weight gain, impotency, and headaches, according to the Sleep Apnea Association of America.

People with sleep apnea often use a CPAP (Continuous Positive Airway Pressure) system to keep air passages open while sleeping. The CPAP system includes a machine to regulate the air pressure delivered to the user through a hose, mask and head gear. There are many styles of masks, and the use of one over the other is determined by a person's preference. There are three types: full face, which covers the user's nose and mouth, over the nose, and "pillow" which has a cannula for each nostril and is associated with a soft form generally known as a pillow. Different styles exist in each type that involve different hose attachment designs.

All systems are vented through an outlet vent to allow carbon dioxide ($CO_2$) from exhalation to exhaust from the system. Air pressure is adjusted for a prescribed amount plus an amount for loss of pressure through the vent. It is common for air to come out of a mask outlet vent at a high flow rate. This exhaust, if directed toward the skin (i.e. an arm) or a sleeping partner, is uncomfortable. It feels cold and is a near continuous, concentrated blast of air that can wake a user from the sleep the machine was designed to obtain. The air flow is also noisy and disturbing to a sleeping partner.

It is therefore a primary object of the present invention to diffuse the high velocity air exhausting through the vent of the CPAP machine while maintaining necessary flow from the vent to prevent backpressure and $CO_2$.buildup. It is a further object to quiet the flow from the outlet vent without introducing back pressure and $CO_2$ buildup. It is another object to employ a diffuser that is easy to use, install and clean. It is a further object that the diffuser be disposable without appreciable cost. For all purposes herein, the term 'disposable" means the diffuser is inexpensive to replace. Inexpensive is deemed to mean the diffuser costs less than about 5% of the cost of the mask.

SUMMARY

The CPAP vent diffuser of the present invention operates to prevent exhausted air and exhaled $CO_2$ from the vent of a mask of a CPAP machine from causing a harsh rush of air being directed at the user or their mate that would disturb sleep without operationally impairing total flow of the expired air. This is done by providing a chamber into which air flows from the vent pushing out the diffuser walls that are larger than the vent through which air passes into the chamber, dispersing the flow of quickly moving air throughout the chamber, which consequently decreases the speed of the air flow to produce a more gentle flow of the exhausting air from the diffuser than from the vent while still allowing the air and exhaled $CO_2$ to escape the CPAP vent without impeding total air flow from the mask.

Typically, a hose connects a CPAP machine to the mask held over the user's nose or nose and mouth. The mask necessarily includes a hose through which air flow is fed into the mask which is exhausted from the mask's outlet vent along with a user's exhalation. For a full face mask and an over the nose mask, commonly, the vent is a hole in the tube extending outward on the mask to which the hose is connected. For a 'pillow' style mask, the vent is on the soft tube called a pillow with the vent directly across from the cannulas which extend from the tube and interface with the user's nose. The air pressure flows into the pillow, from a tube which connects the pillow from the hose.

The CPAP vent diffuser goes over the vent and is made of soft, slightly gathered, porous knit material (like tee shirt material). It is generally a tubular sheath with elastic circumferentially sewn around its ends to hold it in place with an effective air seal around the tube on each end of the vent. (It is recognized that there are numerous other means for closing diffuser ends around a tube; for these purposes, all such other means known in the art are included here by general reference and are deemed included in describing elastic, which is understood to be representative of such other means.) The CPAP vent diffuser allows the expired air with carbon dioxide exhalation to exhaust through the knit material and diffuses the stream of air flow from the mask vent to stop direct venting on the user or on a sleeping partner.

The construction of the CPAP vent diffuser begins with a rectangle of soft, porous, knit material larger in width than the circumference of the hose/tube/vent assembly, gathered at each end with elastic sewn into each end. The elastic is shorter than the cloth is wide so as it is put into the cloth, the cloth will gather. This gathering creates a space or chamber between the tube/vent of the CPAP machine and the diffuser. For a full face mask or over the nose mask use, opposite rectangle edges are then sewn together to form a tube with elastic around each tube end. Construction of the pillow style mask of the CPAP vent diffuser begins with a rectangle of soft, porous, knit material larger in width than the circumference of the hose/tube/vent assembly gathered at each end with elastic sewn into each end. However, in the center of the open rectangle is an oval opening of a size to accommodate the cannula which goes through the open oval before interfacing with the nostrils.

The diffuser is then slipped over hose/tube/mask assembly joint of a full face and nose style mask or the soft tube of a pillow style mask to cover the vent and allow the cannula to fit though the oval opening. Then the air hose is attached to the tube in both styles after the diffuser is installed. Diffusers for both mask styles are easily removed for cleaning and are typically machine washable.

DETAILED DESCRIPTION OF THE PREFERRED EMBODIMENTS

Figure 1:
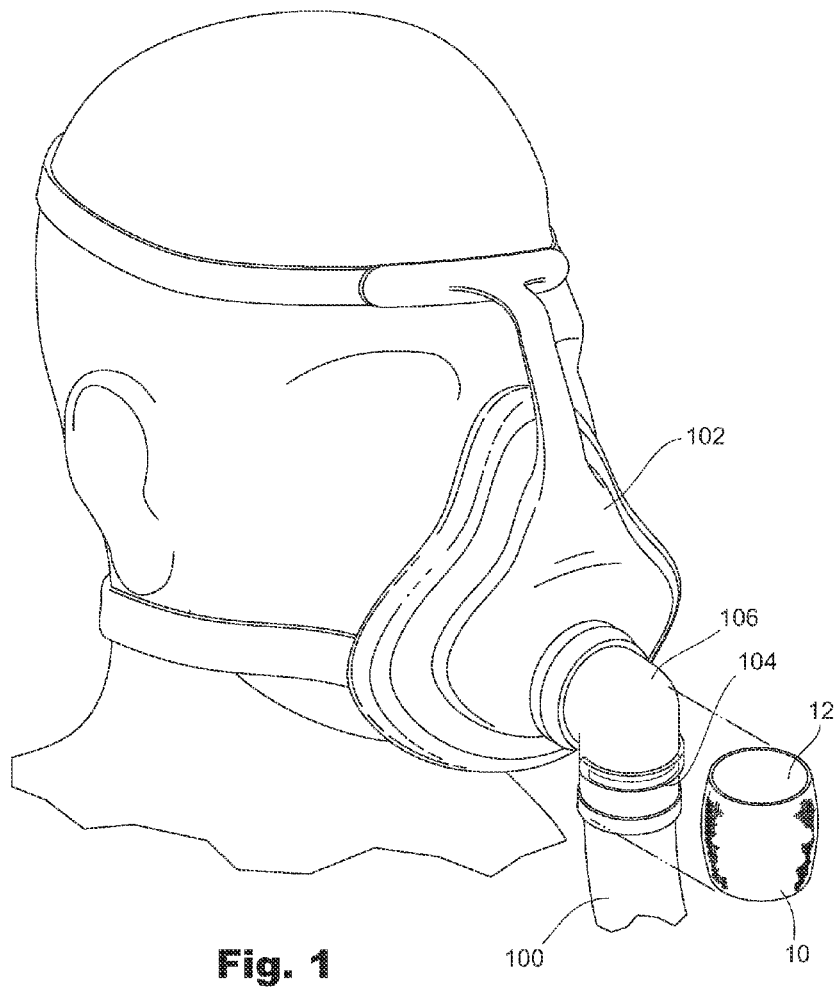
FIG. 1 is a perspective view of a CPAP mask typical of a full face mask of the prior art in use showing a mask vent in a tube extending outward on the mask to which an air hose is attached.
Figure 2:
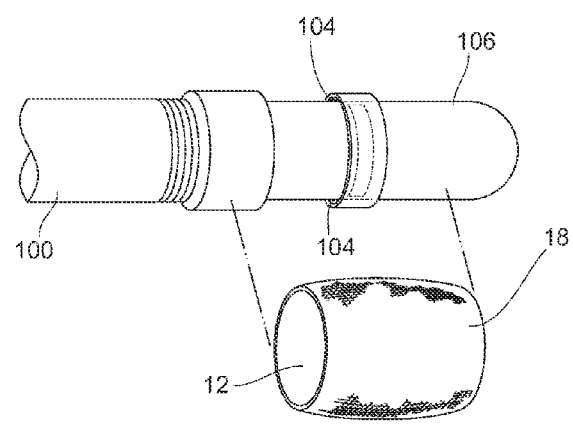
FIG. 2 is a front perspective view of a CPAP mask vent shown with the diffuser of the present invention.
Figure 3:
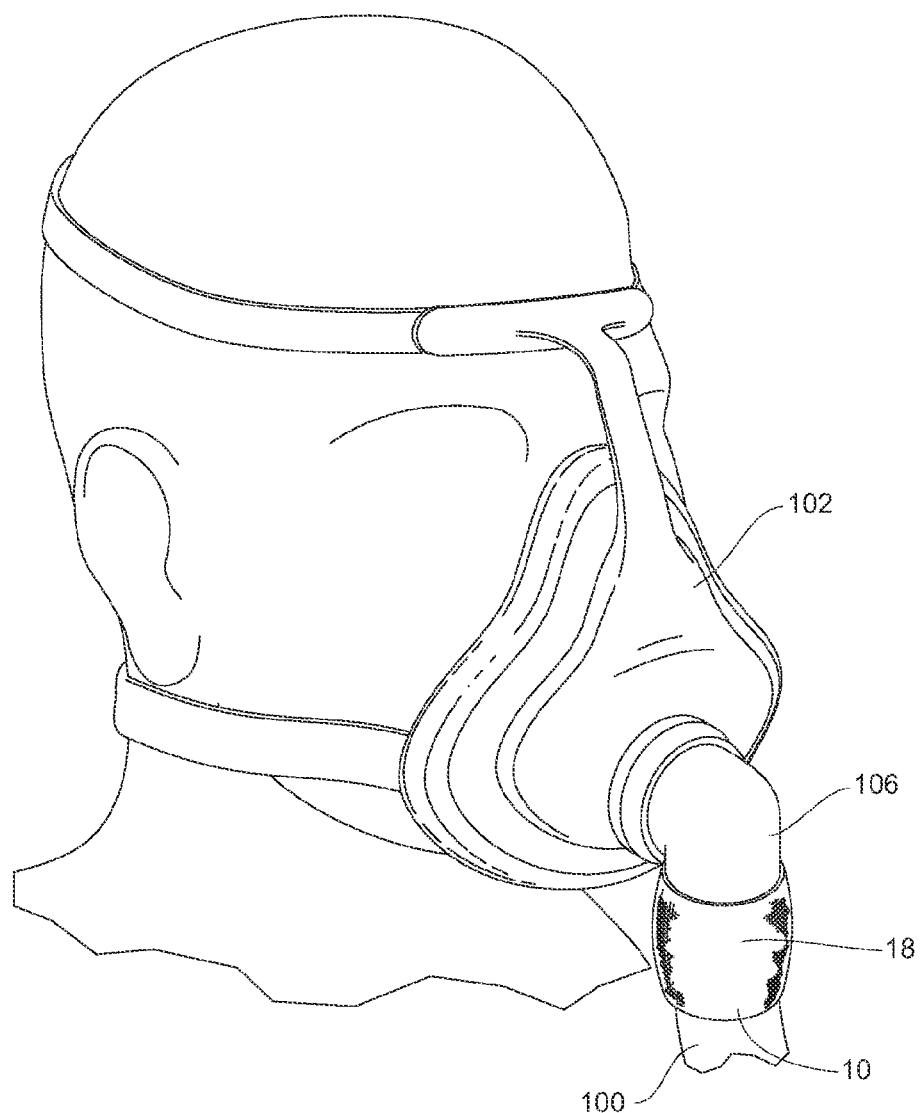
FIG. 3 is a perspective view of the mask of FIG. 1 showing a diffuser of the present invention installed thereon.
Figure 4:
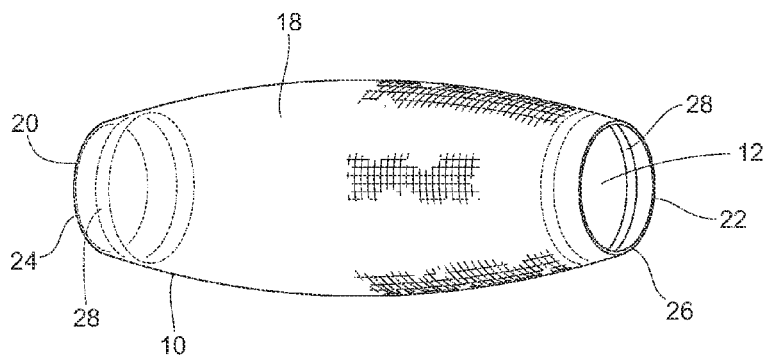
FIG. 4 is a perspective view of the diffuser shown installed in FIG. 2, shown expanded from air pressure within.
Figure 5:
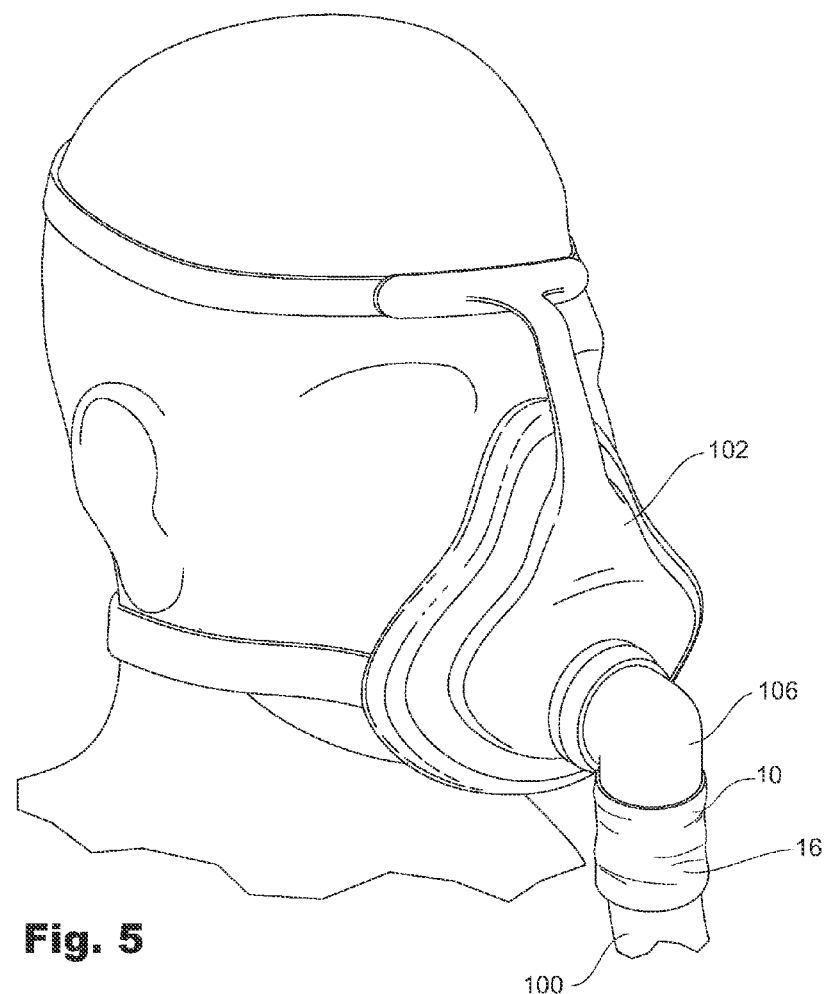
FIG. 5 is a perspective view of the diffuser of FIG. 3 shown collapsed without internal air pressure about the mask tube.
Figure 6:
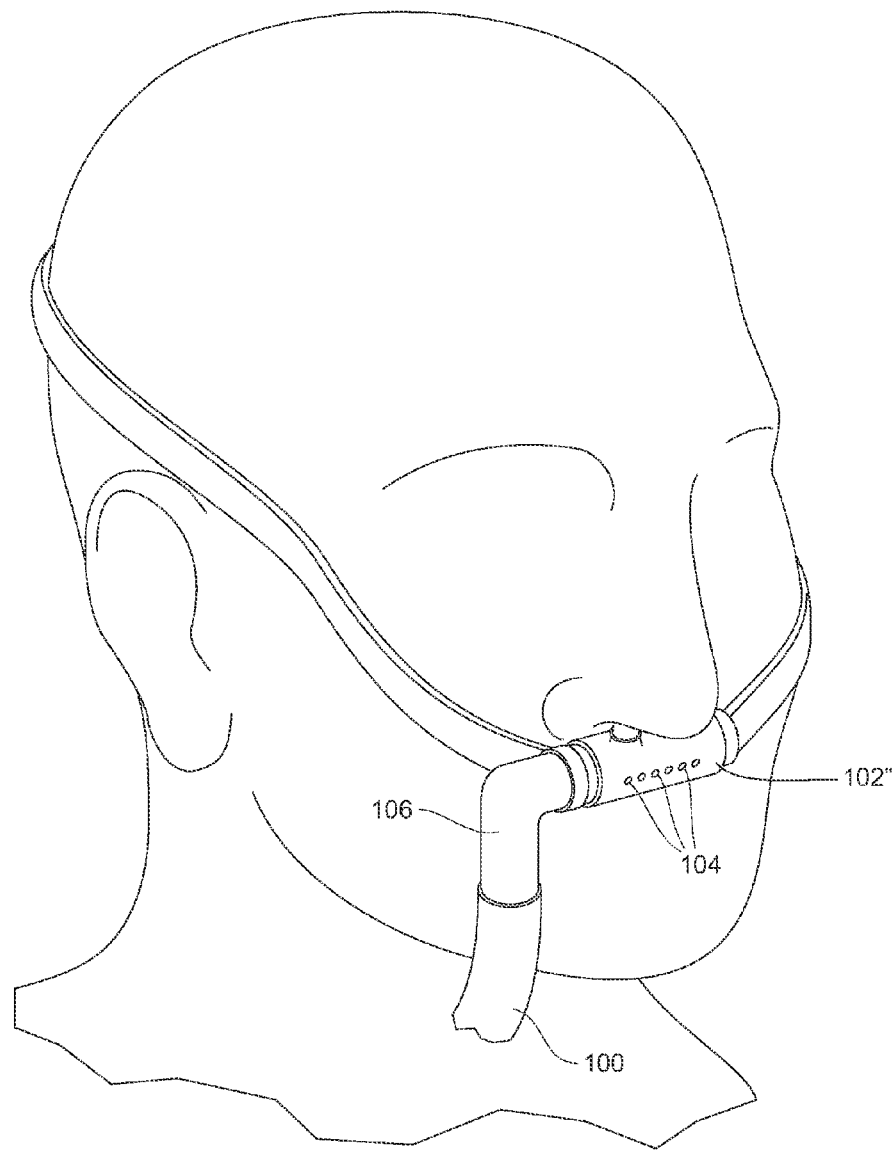
FIG. 6 is a perspective view of a CPAP mask typical of a 'pillow' styled face mask of the prior art in use showing a mask vent in a side of a tube opposite a side of the tube from which cannulas extend for interfacing with a user's nose.
Figure 7:
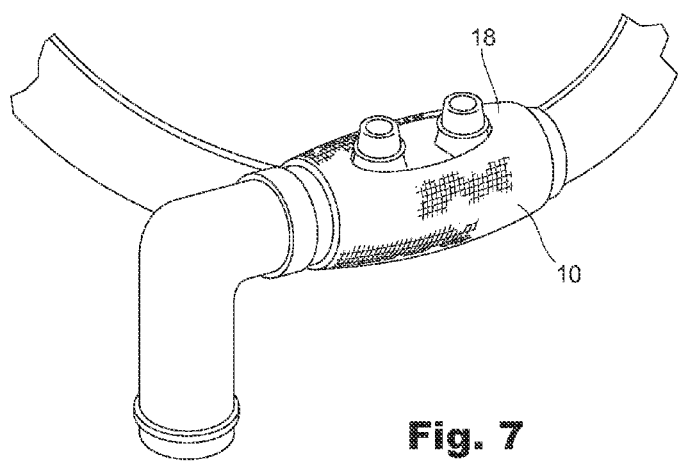
FIG. 7 is a perspective view of the mask of FIG. 5 showing a diffuser of the present invention installed thereon with air pressure from air flow out of the vent inflating the diffuser into a chamber.
Figure 8:
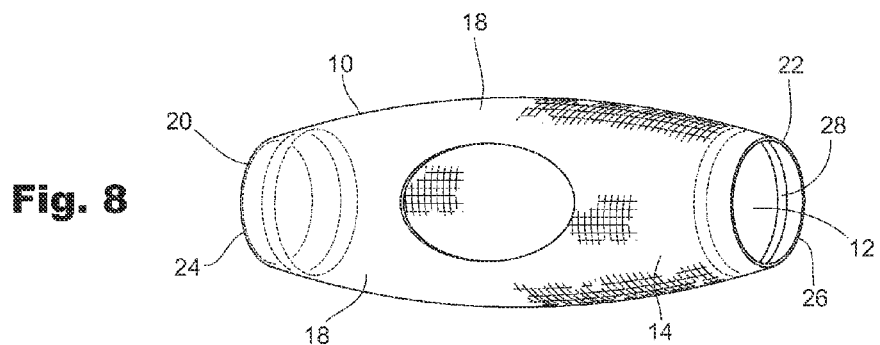
FIG. 8 is a side view of the diffuser of FIG. 6 showing an opening through which cannulas closely fit.
Figure 9:
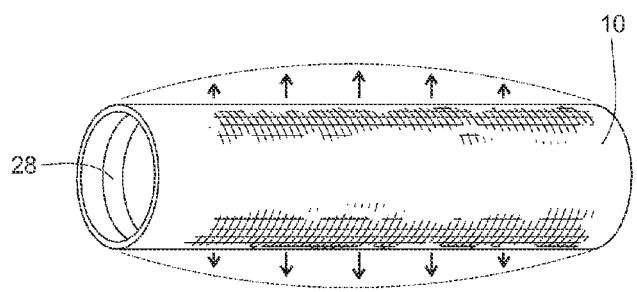
FIG. 9 is a perspective view of the mask of FIG. 3 showing an expandable diffuser with a generally tubular wall.

A CPAP system includes a machine (not shown) that generates air flow with a prescribed air pressure which air is propelled into the hose 100, then through the tube 106, and into a mask 102 that covers a user's nose or nose and mouth for inhalation. The expired air from the mouth or nose of a user that experiences sleep apnea flows back through the mask 102, which feeds the expired air to the tube 106 where the air exits the system through a vent 104. As previously noted, masks are commercially available in several designs and styles, including masks full face masks, over the nose masks, and 'pillow' masks. Such masks for addressing sleep apnea are well known in the art and need not be described separately herein, though the art of sleep apnea masks is deemed included hereby by reference. Of import to this disclosure is that the mask 102 necessarily has an air outlet vent 104 through which expired gases are exhausted from the mask during use.

The diffuser 10 of the present invention comprises a sheath 18 for use with a CPAP mask mask 102 with tube 106 and hose 100 and is adapted to fit around the air vent (or vents) 104 of the mask 102 establishing an effective air seal about the vent 104 such that expired air flowing from the vent 104 is received into the sheath 18. The diffuser 10 presents with a surface area larger than the vent 104 defining a chamber 12 within.

The diffuser 10 is porous such that gases exhausted through the vent 104 are distributed within the chamber 12 and pass out of the chamber 12 moderating gas flow from the vent 104 which passes out of the chamber 12 through the diffuser 10. The diffuser 10 may further comprise collapsing walls 16 and may at least partially inflate away from the vent 104 when expired gases flow into the chamber 12 under pressure of the air flow. The advantage gained is the air flow otherwise discharged directly from the vent 104 at a prescribed air pressure is disturbing outside the diffuser 10 at substantially reduced air flow rate by introducing the diffuser 10 between the vent 104 and the discharge of air to ambient surroundings. The reduced rate of air flow also results in a substantial reduction in noise generated at the vent 104. The chamber 12 serves to absorb acoustic energy generated at the vent 104 as air is discharged from the tube 102 attached to the mask and further air discharged through the diffuser is discharged over a much larger area as the expired gases are exhausted substantially uniformly over the diffuser 10 under equal pressure and therefore at a much reduced flow rate per unit area which also minimizes noise from the air discharge in the ambient surroundings.

The prescribed air pressure coming out of the vent 104 inflates the diffuser 10 creating the chamber 12 such that air flow out of the vent 104 is not substantially inhibited, in which case the diffuser 10 may at least partially inflate during flow of gases from the vent 104 and at least partially deflate during lack of flow from the vent 104 without gas back flowing into the vent 104 from the chamber, although the inflating may be small depending on the rate of flow from the vent 104. The porous diffuser 10 slows the air flow as the air passes through the material.

The diffuser 10 is generally tubular for use with a CPAP mask 102 that has its vent 104 in tube 106 extending from the mask 102, wherein ends 20, 22 of the tubular diffuser are closed on opposite sides 24, 26 of the vent 104 therein closing diffuser 10 about the vent 104. The ends 20, 22 of the tubular diffuser 10 are fit with elastic 28 (or other closing means) such that they expand sufficiently to conveniently slide the diffuser 10 over the tube 106 and the vent 104 in the tube 106 and constrict to close the ends 20, 22 in an effective air seal. Thus, the diffuser 10 is quickly removable by disconnecting the hose 100 from the tube 106, installing the diffuser 10 over the vent 104 and re-installing the hose 100 to the tube 106 without otherwise requiring disassembly of the CPAP system.

It should be appreciated that the diffuser 10 of such simple and inexpensive construction is disposable and amenable to easy cleaning such as washing.

It is to be understood that variations in size, materials, chamber shape and form, general assembly that could be devised in implementing this disclosure are deemed obvious to one skilled in the art. Therefore, the description is considered as representative of these possible variations, which are deemed to be included by the above description of the present invention.

The invention claimed is:

1. A CPAP system improvement comprising, a diffuser, an air input hose connected between a machine that generates air flow and a mask that covers a user's nose or nose and mouth, the mask having a tube with a vent through which expired gases are exhausted from the mask during use, wherein the diffuser is mounted around the vent and is thus adapted to receive air flow out of the vent, wherein the diffuser has a surface area larger than the vent and wherein the diffuser is porous such that gases exhausted through the vent are distributed within and pass through the diffuser, the diffuser therein capturing and moderating gas flow from the vent.

2. The diffuser of claim 1 wherein the diffuser comprises a sheath that fits over the vent and obtains an effective air seal around the vent.

3. The diffuser of claim 2 wherein the sheath is generally tubular for use with a CPAP mask that has its vent in a tube extending from the mask, wherein ends of the tubular sheath are closed on opposite sides of the vent therein closing the sheath about the vent.

4. The diffuser of claim 3 wherein said ends of the tubular sheath are elastic, such that they expand sufficiently to conveniently slide the sheath over the tube and the vent in the tube and constrict to close the ends in an effective air seal around the vent.

5. The diffuser of claim 3 wherein the sheath is of porous fabric having a mesh of size that allows gas to pass out of the chamber such that air flow out of the vent is not substantially inhibited.

6. The diffuser of claim 3 wherein the sheath further comprises collapsing walls inflatable away from the vent when expired air flows into the sheath.

7. The diffuser of claim 6 such that the sheath at least partially inflates during flow of gases from the vent and at least partially deflates during lack of flow from the vent without gas back flowing into the vent from the chamber.

8. The diffuser of claim 1 wherein the expired gases are exhausted from the chamber substantially uniformly through the diffuser.

9. The diffuser of claim 1 wherein a chamber is created under pressure of flow of gases out of the vent, moving the diffuser away from the vent.

10. The diffuser of claim 1 wherein the sheath is of porous fabric having a mesh of size that allows gas to pass out of the chamber at the average rate that air flows into the chamber over a user's breathing cycle such that air flow out of the vent is not substantially inhibited.

11. The diffuser of claim 1 wherein the diffuser comprises a sheath having collapsing walls that can inflate away from the vent when expired air flows into the diffuser forming a chamber within the sheath.

12. The diffuser of claim 11 such that the sheath at least partially inflates during flow of air from the vent and at least partially deflates during reduction of flow from the vent without air back flowing into the vent from the chamber.

13. The diffuser of claim 1 wherein the diffuser is disposable.

* * * * *